(12) United States Patent
Whipple

(10) Patent No.: US 8,133,262 B2
(45) Date of Patent: Mar. 13, 2012

(54) LARGE DIAMETER BONE ANCHOR ASSEMBLY

(75) Inventor: Dale E. Whipple, East Taunton, MA (US)

(73) Assignee: DePuy Spine, Inc., Raynham, MA (US)

( * ) Notice: Subject to any disclaimer, the term of this patent is extended or adjusted under 35 U.S.C. 154(b) by 577 days.

(21) Appl. No.: 11/741,161

(22) Filed: Apr. 27, 2007

(65) Prior Publication Data

US 2008/0015579 A1 Jan. 17, 2008

Related U.S. Application Data

(60) Provisional application No. 60/795,945, filed on Apr. 28, 2006.

(51) Int. Cl.
*A61B 17/70* (2006.01)

(52) U.S. Cl. ........ 606/269; 606/265; 606/266; 606/267; 606/300

(58) Field of Classification Search .................. 606/246, 606/264–276, 300–321, 60, 61, 278, 279, 606/364; 411/16, 136, 151, 190
See application file for complete search history.

(56) References Cited

U.S. PATENT DOCUMENTS

| | | | |
|---|---|---|---|
| 5,181,917 A | 1/1993 | Rogozinski |
| 5,242,443 A | 9/1993 | Kambin |
| 5,443,467 A | 8/1995 | Biedermann |
| 5,501,684 A | 3/1996 | Schlapfer |
| 5,584,831 A | 12/1996 | McKay |
| 5,589,684 A | 12/1996 | Ventrudo |
| 5,591,166 A | 1/1997 | Bernhardt |
| 5,647,873 A | 7/1997 | Errico |
| 5,669,911 A | 9/1997 | Errico |
| 5,672,176 A | 9/1997 | Biedermann |
| 5,688,274 A | 11/1997 | Errico |
| 5,690,630 A | 11/1997 | Errico |
| 5,725,528 A | 3/1998 | Errico |
| 5,728,098 A | 3/1998 | Sherman |
| 5,733,285 A | 3/1998 | Errico |
| 5,735,851 A | 4/1998 | Errico |
| 5,782,833 A | 7/1998 | Haider |
| 5,790,543 A | 8/1998 | Cloutier |
| 5,797,911 A | 8/1998 | Sherman |
| 5,810,819 A | 9/1998 | Errico |
| 5,817,094 A | 10/1998 | Errico |

(Continued)

FOREIGN PATENT DOCUMENTS

CN 201085681 7/2008

(Continued)

OTHER PUBLICATIONS

Harms, "Posterior C1-C2 Fusion With Polyaxial Screw and Rod Fixation"; Spine; Nov. 15, 2001, pp. 2467-2471; vol. 26(22); Lippincott Williams & Wilkins.

(Continued)

*Primary Examiner* — Eduardo C Robert
*Assistant Examiner* — Christina Negrelli

(57) ABSTRACT

Bone anchor assemblies having a large diameter for fixing a spinal connection element to bone and methods of assembly are described. The assembly includes a receiver member for receiving the spinal connection element, a bone-engaging shank for engaging bone, a retaining member for retaining the head of the shank within the receiver member and a locking member for locking the retaining member within the receiver member.

15 Claims, 7 Drawing Sheets

U.S. PATENT DOCUMENTS

| | | | |
|---|---|---|---|
| 5,863,293 A | 1/1999 | Richelsoph | |
| 5,879,350 A | 3/1999 | Sherman | |
| 5,882,350 A | 3/1999 | Ralph | |
| 5,885,286 A | 3/1999 | Sherman | |
| 5,891,145 A | 4/1999 | Morrison | |
| 5,902,303 A | 5/1999 | Eckhof | |
| 5,910,142 A | 6/1999 | Tatar | |
| 5,954,725 A | 9/1999 | Sherman | |
| 5,964,760 A | 10/1999 | Richelsoph | |
| 5,997,539 A | 12/1999 | Errico | |
| 6,010,503 A | 1/2000 | Richelsoph | |
| 6,022,350 A | 2/2000 | Ganem | |
| 6,053,917 A | 4/2000 | Sherman | |
| 6,063,090 A | 5/2000 | Schlapfer | |
| 6,090,110 A | 7/2000 | Metz-Stavenhagen | |
| 6,113,601 A | 9/2000 | Tatar | |
| 6,132,432 A | 10/2000 | Richelsoph | |
| 6,132,434 A | 10/2000 | Sherman | |
| 6,146,383 A | 11/2000 | Studer | |
| 6,183,472 B1 | 2/2001 | Lutz | |
| 6,214,006 B1 | 4/2001 | Metz-Stavenhagen | |
| 6,248,105 B1 | 6/2001 | Schlapfer | |
| 6,254,602 B1 | 7/2001 | Justis | |
| 6,261,287 B1 | 7/2001 | Metz-Stavenhagen | |
| 6,280,442 B1 | 8/2001 | Barker | |
| 6,287,311 B1 | 9/2001 | Sherman | |
| 6,355,040 B1 | 3/2002 | Richelsoph | |
| RE37,665 E | 4/2002 | Ralph | |
| 6,371,957 B1 | 4/2002 | Amrein | |
| 6,402,752 B2 | 6/2002 | Schäffler-Wachter | |
| 6,454,773 B1 | 9/2002 | Sherman | |
| 6,471,705 B1 | 10/2002 | Biedermann | |
| 6,482,207 B1 | 11/2002 | Errico | |
| 6,485,494 B1 | 11/2002 | Haider | |
| 6,488,681 B2 | 12/2002 | Martin | |
| 6,520,963 B1 | 2/2003 | McKinley | |
| 6,537,276 B2 | 3/2003 | Metz-Stavenhagen | |
| 6,554,834 B1 | 4/2003 | Crozet | |
| 6,565,567 B1 | 5/2003 | Haider | |
| 6,582,436 B2 | 6/2003 | Schlapfer | |
| 6,660,004 B2 | 12/2003 | Barker | |
| 6,672,788 B2 | 1/2004 | Hathaway | |
| 6,716,214 B1 | 4/2004 | Jackson | |
| 6,723,100 B2 | 4/2004 | Biedermann | |
| 6,835,196 B2 | 12/2004 | Biedermann | |
| 6,869,433 B2 | 3/2005 | Glascott | |
| 6,881,215 B2 | 4/2005 | Assaker | |
| 6,887,242 B2 | 5/2005 | Doubler | |
| 6,905,500 B2 | 6/2005 | Jeon | |
| 7,022,122 B2 | 4/2006 | Amrein | |
| RE39,089 E | 5/2006 | Ralph | |
| 7,090,674 B2 | 8/2006 | Doubler | |
| 7,186,255 B2 | 3/2007 | Baynham | |
| 7,306,606 B2 | 12/2007 | Sasing | |
| 7,322,981 B2 | 1/2008 | Jackson | |
| 7,604,655 B2 | 10/2009 | Warnick | |
| 7,625,396 B2 | 12/2009 | Jackson | |
| 7,662,172 B2 | 2/2010 | Warnick | |
| 8,012,185 B2 | 9/2011 | Warnick | |
| 2002/0151900 A1 | 10/2002 | Glascott | |
| 2002/0183748 A1 | 12/2002 | Martin | |
| 2003/0004512 A1* | 1/2003 | Farris et al. | 606/61 |
| 2003/0032957 A1 | 2/2003 | McKinley | |
| 2003/0125741 A1 | 7/2003 | Biedermann | |
| 2003/0149432 A1 | 8/2003 | Frigg | |
| 2004/0097933 A1 | 5/2004 | Lourdel | |
| 2004/0102781 A1 | 5/2004 | Jeon | |
| 2004/0106925 A1 | 6/2004 | Culbert | |
| 2004/0127899 A1 | 7/2004 | Konieczynski | |
| 2004/0158247 A1 | 8/2004 | Sitiso | |
| 2004/0236330 A1 | 11/2004 | Purcell | |
| 2004/0267264 A1 | 12/2004 | Konieczynski | |
| 2005/0049588 A1 | 3/2005 | Jackson | |
| 2005/0049589 A1 | 3/2005 | Jackson | |
| 2005/0055026 A1 | 3/2005 | Biedermann | |
| 2005/0080415 A1 | 4/2005 | Keyer | |
| 2005/0096654 A1 | 5/2005 | Lin | |
| 2005/0154391 A1 | 7/2005 | Doherty | |
| 2005/0171542 A1 | 8/2005 | Biedermann | |
| 2005/0273101 A1 | 12/2005 | Schumacher | |
| 2005/0277928 A1 | 12/2005 | Boschert | |
| 2006/0036252 A1 | 2/2006 | Baynham | |
| 2006/0084981 A1* | 4/2006 | Shluzas | 606/61 |
| 2006/0100621 A1 | 5/2006 | Jackson | |
| 2006/0100622 A1 | 5/2006 | Jackson | |
| 2006/0149231 A1 | 7/2006 | Bray | |
| 2006/0149232 A1 | 7/2006 | Sasing | |
| 2006/0149240 A1 | 7/2006 | Jackson | |
| 2006/0149244 A1 | 7/2006 | Amrein | |
| 2006/0190002 A1 | 8/2006 | Tallarida | |
| 2006/0247631 A1 | 11/2006 | Ahn | |
| 2006/0293659 A1 | 12/2006 | Alvarez | |
| 2007/0049933 A1 | 3/2007 | Ahn | |
| 2007/0055240 A1 | 3/2007 | Matthis | |
| 2007/0118117 A1 | 5/2007 | Altarac | |
| 2007/0191835 A1 | 8/2007 | Justis | |
| 2007/0233078 A1 | 10/2007 | Justis | |
| 2008/0004625 A1 | 1/2008 | Runco | |
| 2008/0015576 A1 | 1/2008 | Whipple | |
| 2008/0015579 A1 | 1/2008 | Whipple | |
| 2008/0015580 A1 | 1/2008 | Chao | |
| 2008/0015596 A1 | 1/2008 | Whipple | |
| 2008/0015597 A1 | 1/2008 | Whipple | |
| 2008/0125816 A1 | 5/2008 | Jackson | |
| 2008/0132957 A1 | 6/2008 | Matthis | |
| 2008/0234761 A1 | 9/2008 | Jackson | |
| 2008/0269809 A1 | 10/2008 | Garamszegi | |
| 2008/0287998 A1 | 11/2008 | Doubler | |
| 2009/0036934 A1 | 2/2009 | Biedermann | |

FOREIGN PATENT DOCUMENTS

| | | |
|---|---|---|
| EP | 0732081 | 9/1996 |
| EP | 836835 | 4/1998 |
| EP | 1090595 | 4/2001 |
| WO | WO 199702786 | 1/1997 |
| WO | WO 9832386 | 7/1998 |
| WO | WO 9852482 | 11/1998 |
| WO | WO 2004041100 | 5/2004 |
| WO | WO 2006047707 | 5/2006 |

OTHER PUBLICATIONS

Stokes, "Posterior Atlantoaxial Stabilization New Alternative to C1-C2 Transarticular Screw"; Neurosurg Focus; Jan. 15, 2002, pp. 1-5; vol. 12(1); Article 6.

Mumaneni, "Posterior Cervical Fixation Using a New Polyaxial Screw and System: Technique and Surgical Results"; Neurosurg Focus; Jan. 15, 2002, pp. 1-5; vol. 12(1); Article 8.

Schultheiss, "MACS TL Polyaxialscrew XL A New Concept to Increase the Stability of Ventral Spondylodesis in the Presence of Dorsal Structure Injuries"; Orthopade; Apr. 2002, pp. 397-401; vol. 31(4); Springer-Verlag.

Fogel, "Physical Characteristics of Polyaxial-Headed Pedicle Screws and Biochemical Comparison of Load with Their Failure"; Spine; Mar. 1, 2003, pp. 397-401; vol. 28(5); Lippincott Williams & Wilkins.

Stulik, "Combined Atlantoaxial Fractures"; Acta Chir Orthop Traumatol Cech; 2005; pp. 105-110; vol. 72(2).

McGee, "A Simplified Galveston Technique for the Stabilization of Pathological Fractures of the Sacrum"; Eur. Spine J., 2009; pp. 451-454; vol. 9.

Baldwin, "Sacral Fixation Using Iliac Instrumentation and a Variable-Angle Screw Device", J. Neurosurg; 1994; pp. 3134-316; vol. 81.

* cited by examiner

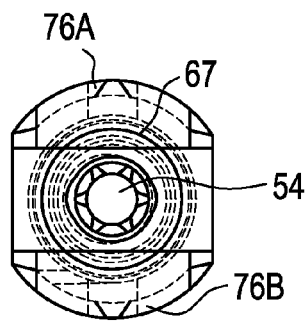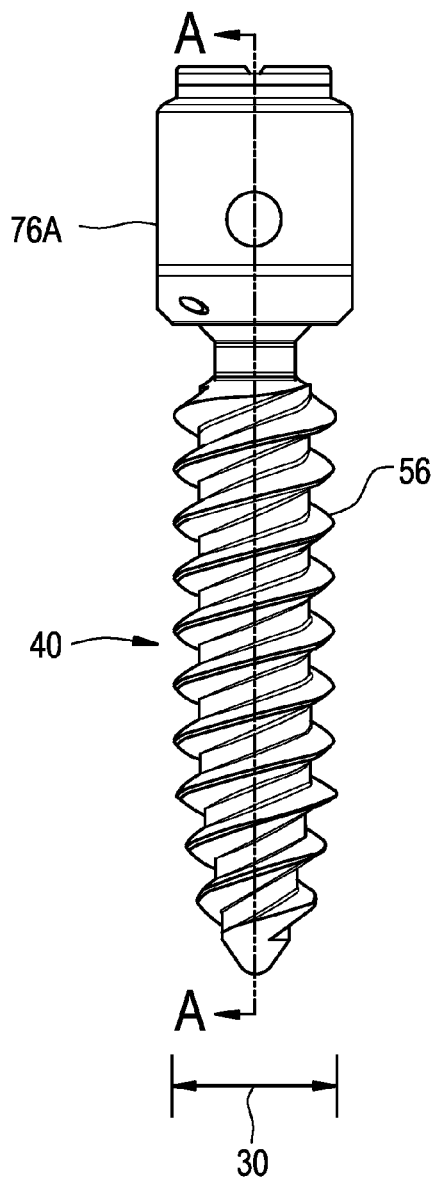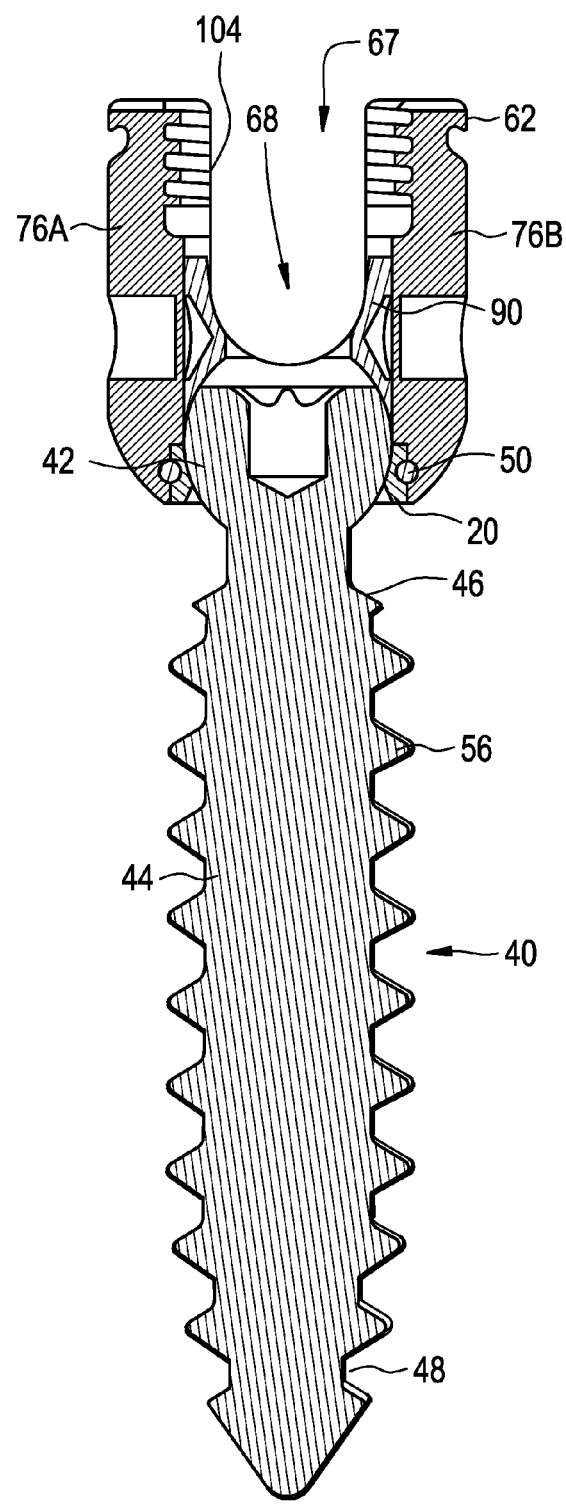

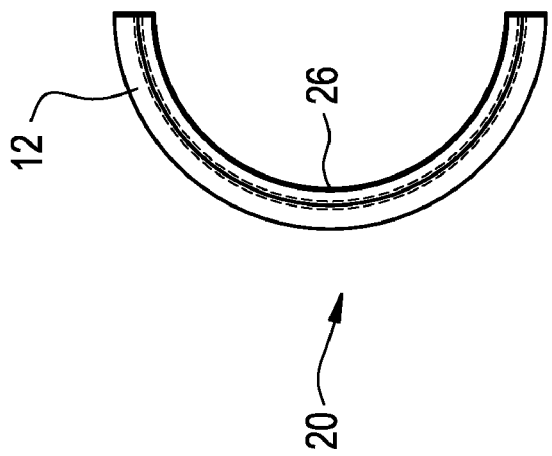
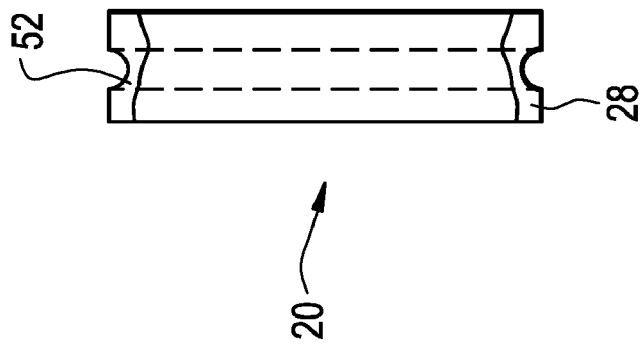
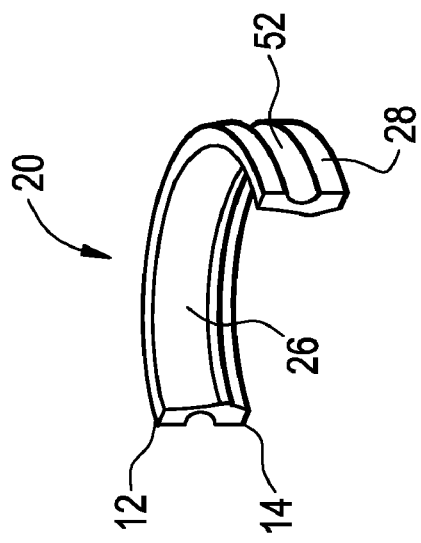

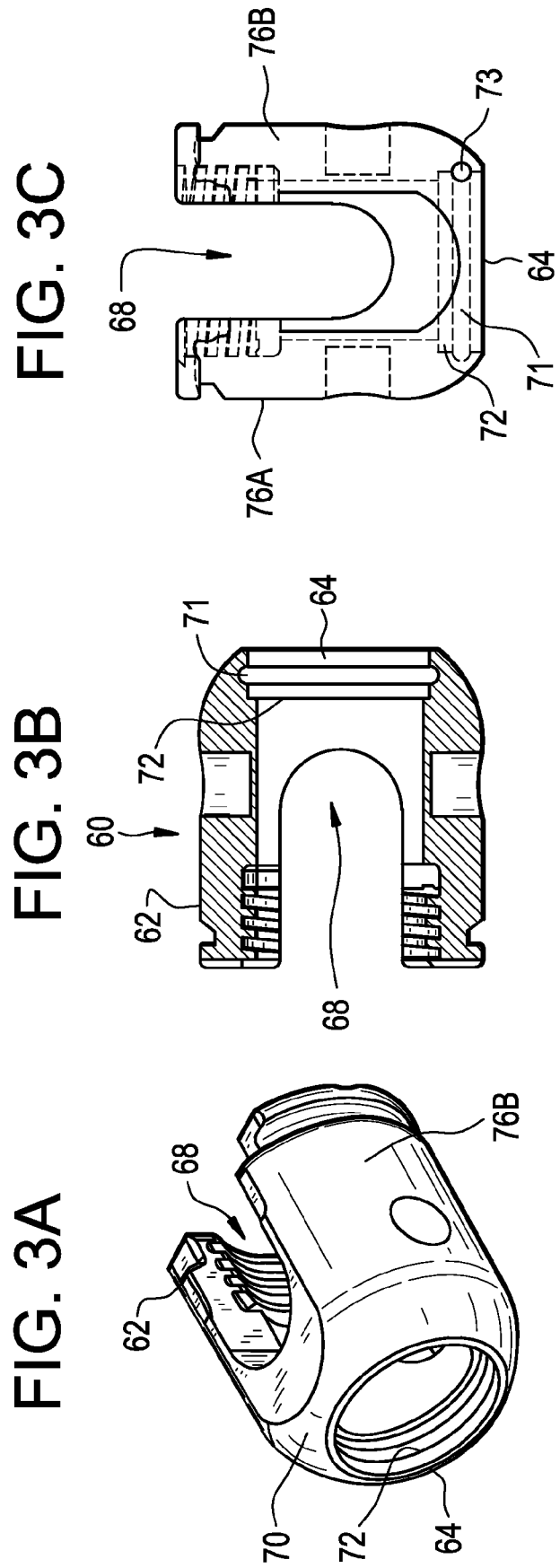

LARGE DIAMETER BONE ANCHOR ASSEMBLY

CONTINUING DATA

This application claims the benefit of U.S. Provisional Patent Application Ser. No. 60/795,945, entitled "Large Diameter Bone Anchor Assembly", filed Apr. 28, 2006, which is hereby incorporated herein by reference.

BACKGROUND

Spinal connection systems may be used in orthopedic surgery to align and/or fix a desired relationship between adjacent vertebrae. Such systems typically include a spinal connection element, such as a relatively rigid fixation rod or plate or a dynamic connector, that is coupled to adjacent vertebrae by attaching the element to various anchoring devices, such as hooks, bolts, wires, or screws. The spinal connection element can have a predetermined contour that has been designed according to the properties of the target implantation site, and once installed, the spinal connection element holds the vertebrae in a desired spatial relationship, either until desired healing or spinal fusion has taken place, or for some longer period of time.

Spinal connection elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal connection element receiving portion, which, in spinal rod applications, is usually in the form of a U-shaped slot formed in the head for receiving the rod. A set-screw, plug, cap or similar type of closure mechanism, may be used to lock the connection element into the connection element receiving portion of the pedicle screw. In use, the shank portion of each screw may be threaded into a vertebra, and once properly positioned, a connection element may be seated through the spinal connection element receiving portion of each screw and the connection element is locked in place by tightening a cap or similar type of closure mechanism to securely interconnect each screw and the connection element. Other anchoring devices also include hooks and other types of bone screws.

In certain procedures, such as those in the lumbar or sacral spine, it may be necessary to use a larger diameter pedicle screw capable of carrying large loads or engaging large pedicles. A difficulty in using a larger diameter screw comes from the corresponding increase in the size of the receiver head to accommodate the larger diameter screw shank, since the shank is usually assembled from the top through the opening at the proximal end of the receiver head. The increased size of the receiver head can interfere with the bony anatomy and can limit the polyaxial range of motion of the screw head. Another problem associated with manufacturing large diameter top-loading screws is that the opening in the receiver head has to be larger to accept the larger diameter screw shank, which creates the need for a larger closure mechanism. It is desirable to maintain the same size opening in the receiver head such that the same size closure mechanisms can be used. Accordingly, a larger diameter polyaxial screw is needed which is not top-loading.

SUMMARY

Disclosed herein are embodiments of a bottom-loading bone anchor assembly having a large diameter shank. In one embodiment, the bone anchor assembly for engagement to a connection element includes a receiver member having an opening at the proximal end for receiving the connection element and a bore at the distal end leading to a seat portion having a groove; a bone-engaging shank having a head at a proximal end, the head sized to fit within the bore the receiver member; a retaining member having an outer surface shaped to fit within the seat portion of the receiver member and an inner surface shaped to accommodate the head of the bone-engaging shank; and a locking member shaped to fit within the groove of the seat portion and lock the retaining member within the seat portion of the receiver member.

A method of assembly of a bone anchor assembly is disclosed including inserting a bone-engaging shank having a head proximally through a bore of a receiver member having an opening for receiving a spinal connection element; positioning a retaining member around the head of the shank within a seat portion of the receiver member; and advancing a locking member into a groove within the seat portion of the receiver member to lock the retaining member within the receiver member.

BRIEF DESCRIPTION OF THE FIGURES

These and other features and advantages of the bone anchor assembly and methods disclosed herein will be more fully understood by reference to the following detailed description in conjunction with the attached drawings in which like reference numerals refer to like elements through the different views. The drawings illustrate principles of the bone anchor assembly and methods disclosed herein and, although not to scale, show relative dimensions.

FIG. 1B illustrates a top view of the bone anchor assembly shown in FIG. 1A.

FIG. 1C illustrates a side view of the bone anchor assembly shown in FIG. 1A.

FIG. 1D illustrates a cross-section of the bone anchor assembly shown in FIG. 1C.

FIG. 2A illustrates a perspective view of the retaining member of the bone anchor assembly shown in FIG. 1A.

FIG. 2B illustrates a cross-section view of the retaining member of the bone anchor assembly shown in FIG. 2A.

FIG. 2C illustrates a top view of the retaining member shown in FIG. 2A.

FIG. 3A illustrates an isometric view of the receiver member of the bone anchor assembly shown in FIG. 1A.

FIG. 3B illustrates a cross-section view of the receiver member shown in FIG. 3A.

FIG. 3C illustrates a side view with hidden lines of the receiver member shown in FIG. 3A.

DETAIL DESCRIPTION OF EXEMPLARY EMBODIMENTS

Figure 1A:
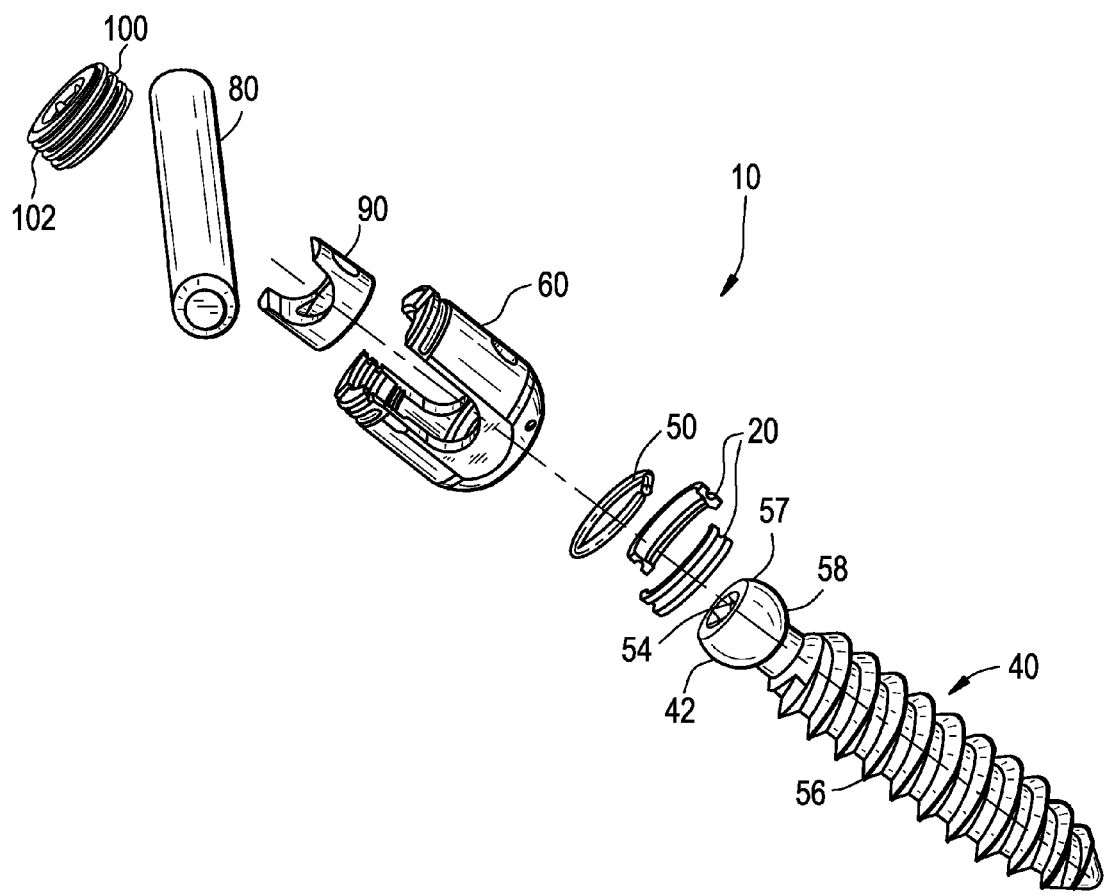
FIG. 1A illustrates an exploded view of a large diameter bone anchor assembly.

Certain exemplary embodiments will now be described to provide an overall understanding of the principles of the structure, function, manufacture, and use of the large diameter bone anchor assembly and methods disclosed herein. One or more examples of these embodiments are illustrated in the accompanying drawings. Those of ordinary skill in the art will understand that the large diameter bone anchor assembly and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a bottom-loading large diameter bone anchor assembly. The exemplary bone anchor assembly 10 may be employed to engage one or more spinal connection elements to bone. For example, bone anchor assembly 10 may be employed to connect a spinal plate, rod (rigid or dynamic), and/or cable to a vertebra of the spine. Although the exemplary bone anchor assembly 10 described below is designed primarily for use in spinal applications, one skilled in the art will appreciate that the structure, features, and principles of the exemplary bone anchor assembly 10, as well as the other exemplary embodiments described below, may be employed to couple any type of orthopedic implant to any type of bone or tissue. Non-limiting examples of applications of the bone connection anchor assembly 10 described herein include long bone fracture fixation/stabilization, small bone stabilization, lumbar spine as well as thoracic stabilization/fusion, cervical spine compression/fixation, dynamic, non-fusion applications including facet replacement and dynamic posterior systems as well as skull fracture/reconstruction plating.

The illustrated exemplary bone anchor assembly 10 includes a bone-engaging shank 40 configured for engaging bone, a receiver member 60 for receiving a spinal connection element, and a retaining member 20 for retaining the shank 40 within the receiver member 60 and a locking member 50 for locking the retaining member 20 within the receiver member 60. The bone-engaging shank 40 extends from a proximal end 46 to a distal end 48 along a longitudinal axis. An outer surface 44 of the bone-engaging shank 40 extends between the proximal end 46 and the distal end 48. The outer surface 44 of the bone-engaging shank 40 may include one or more bone engagement mechanisms to facilitate gripping engagement of the bone anchor assembly 10 to bone. In the illustrated exemplary embodiment, for example, the bone-engaging shank 40 includes an external thread 56. The external thread 56 may extend along at least a portion of the bone-engaging shank 40. For example, in the illustrated exemplary embodiment, the external thread 56 extends from the distal end 48 to the proximal end 46 of the bone-engaging shank 40. One skilled in the art will appreciate that bone engagement mechanisms other than external thread 56 may be employed, including, for example, one or more annular ridges, multiple threads, dual lead threads, variable pitched threads, and/or any other conventional bone engagement mechanism. In the illustrated exemplary embodiment, the shank diameter 30 of bone-engaging shank 40 may be defined by the major diameter of external thread 56.

The proximal end 46 of the exemplary bone-engaging shank 40 has a head 42 configured to fit within the receiver member 60 and to facilitate adjustment of the shank 40 relative to the receiver member 60. For example, the head 42 may be generally spherical in shape to permit pivoting of the bone-engaging shank 40 relative to the receiver member 60. In the illustrated exemplary embodiment, for example, the head 42 may be in the shape of a truncated sphere having a generally planar proximal surface 57 and a generally hemispherically shaped distal surface 58. The head 42 of the shank 40 may have surface texturing, knurling, and/or ridges. A drive feature 54 may be located internally or externally on the head 42 of the shank 40.

Referring to FIGS. 3A-C, the receiver member 60 of the exemplary bone anchor assembly 10 includes a proximal end 62 having a cylindrical opening 67 leading to recess 68, and a distal end 70 having a bore 64 forming a seat portion 72. The receiver member 60, in certain exemplary embodiments, may be configured to receive a spinal connection element and couple the spinal connection element to the bone anchor assembly. In the exemplary embodiment, for example, the recess 68 of the receiver member 60 may be sized and shaped to receive a spinal rod 80, as illustrated in FIG. 1A. For example, the receiver member 60 has a generally U-shaped cross-section defined by two legs 76A and 76B separated by recess 68. Each leg 76A, 76B is free at the proximal end 62 of the receiver member 60. In the exemplary embodiment, for example, the inner surfaces of the legs 76A, 76B are threaded to mate with a corresponding thread on the closure mechanism shown as a setscrew. The exemplary spinal rod 80 may be seated within the recess 68 by aligning the spinal rod 80 and the recess 68, and advancing the spinal rod 80 between the legs 76A, 76B into the recess 68. The configuration of recess 68 of the receiver member 60 may be varied to accommodate the type, size and shape of spinal connection element employed.

In the exemplary embodiment, the distal end 70 of the receiver member 60 forms a seat portion 72 accessible through bore 64 of the receiver member 60. The bore 64 is sized to allow at least a portion of a bone anchor assembly, such as the head 42 of the shank 40 to pass through the bore 64 into the seat portion 72. For example, the head 42 of the shank 40 may be inserted in the proximal direction through the bore 64 of the receiver member 60, as illustrated in FIG. 1A. The diameter of the bore 64 may be greater than the diameter of the cylindrical opening 67 of the receiver member at the proximal end 62. Within the seat portion 72, a groove 71 extends around the circumference of the receiver member 60 shaped to receive the locking member 50 described in more detail below. The groove 71 may have a generally semi-spherical shape and have a diameter greater than the bore 64 and the seat portion 72 as shown in FIG. 3B. The groove 71 is accessible through opening 73 formed in the distal end of leg 76B of the receiver member 60 as shown in FIG. 3C. In some exemplary embodiments, the seat portion 72 may be shaped analogous to the outer surface 28 of the retaining member 20.

In some exemplary embodiments, the seat portion 72 may be generally spherical in shape to permit pivoting of the bone-engaging shank 40 relative to the receiver member 60. In other exemplary embodiments, the seat portion 72 may be tapered or may have any other shape that allows adjustment of the head 42 of the shank 40 and the retaining member 20 relative to the receiver member 60. In the exemplary embodiment, the bone anchor assembly 10 is a polyaxial bone anchor assembly. The bone-engaging shank 40 when assembled within the receiver member 60 may be pivoted to one or more angles relative to the receiver member 60.

Referring to FIG. 1D, retaining member 20 of the bone anchor assembly 10 is positionable within the seat portion 72 of the receiver member 60. The retaining member 20 illustrated in FIGS. 2A-C extends from a proximal end 12 to a distal end 14. The retaining member 20 retains the head 42 of the shank 40 within the receiver member 60. The retaining member 20 may have a generally circular shape including an inner surface 26 contoured for engaging the head 42 of the shank 40 and an outer surface 28 for engaging a portion of the seat portion 72 of the receiver member 60. The inner surface 26 may have a spherical shape in the exemplary embodiment, allowing pivoting between the head 42 of the shank 40 and the receiver member 60. The proximal 12 and distal 14 ends of the outer surface 28 of the retaining member 20 are shaped to fit within the seat portion 72 of the receiver member 60. In one embodiment, the outer surface 28 of the retaining member 20 may have a groove 52 extending around the mid-portion of the retaining member 20 as illustrated in FIG. 2A. The groove 52 may have a cylindrical shape or any other shape such as circular, square, hexagon, ellipse shape to accommodate a portion of the locking member 50. The retaining member 20 may be in the form of a C-shaped ring or may be a half of a ring as shown in FIG. 2A. If the retaining member 20 is in the shape of a half ring, two retaining members 20 are used in the assembly. In one embodiment, the retaining member 20 is positioned within the seat portion 72 of the receiver member 60 such that the groove 52 aligns with the groove 71 of the seat portion 72 to form a cylindrical channel to accommodate the locking member 50.

Figure 4A:
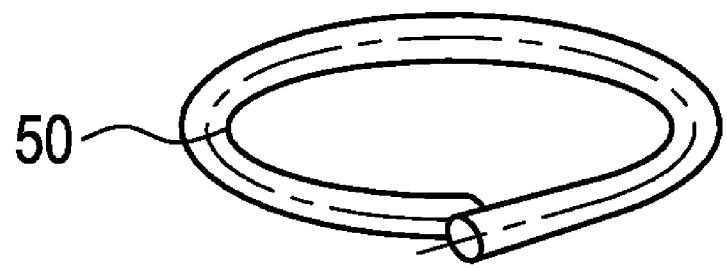
FIG. 4A illustrates a perspective view of the locking member of the bone anchor assembly shown in FIG. 1A.
Figure 4B:
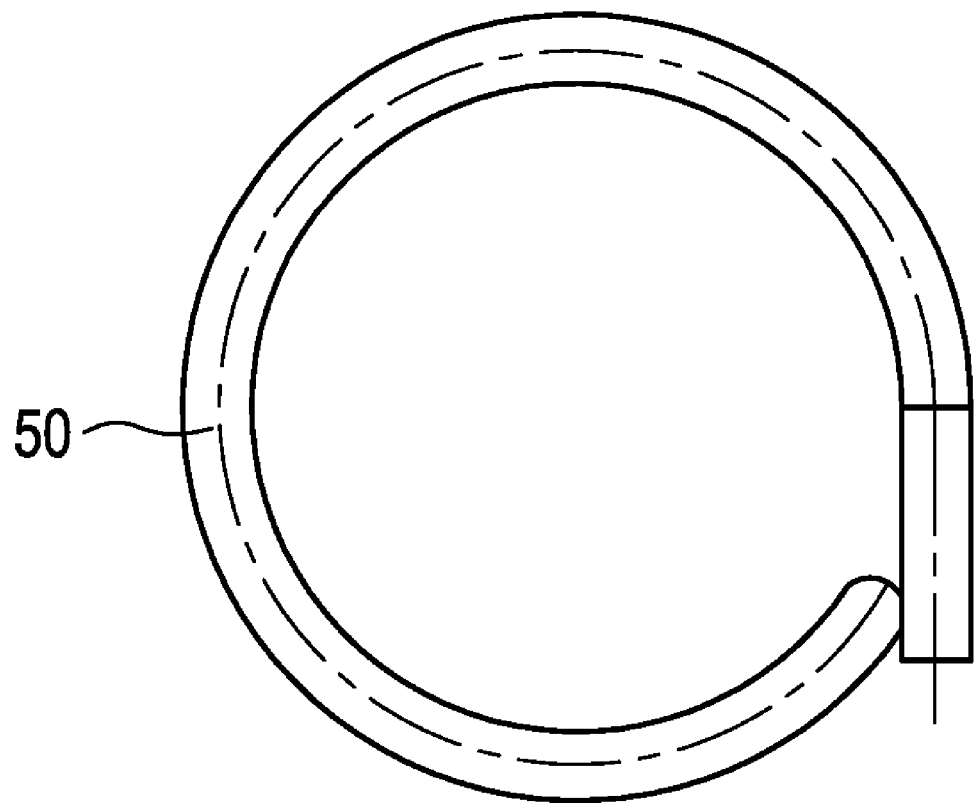
FIG. 4B illustrates a top view of the locking member shown in FIG. 4A.

As shown in FIG. 4A, the locking member 50 of the exemplary embodiment may have a generally circular shape in cross section and may be arcuate in shape, for example, circular, c-shaped or the like. The locking member 50 is positionable within the groove 71 of the seat portion 72 and the groove 52 of the retaining member by accessing the opening 73 in the receiver member 60. The locking member 50 may be a wire, cable, thread, fiber, or any other rigid material including non-corrosive metals and polymers. In alternative embodiments, the locking member may be two or more pins or rods having a circular, rectilinear, oval or other suitable shape in cross section. The pins/rods be linear and/or arcuate along their length and may be inserted through openings in the receiver member communicating with the bore 64 to inhibit the retaining member 20 from moving relative to the receiver member 60.

Figure 5A:
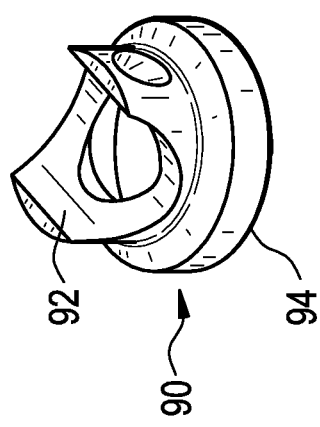
FIG. 5A illustrates a perspective view of the compression member of the bone anchor assembly shown in FIG. 1A.
Figure 5B:
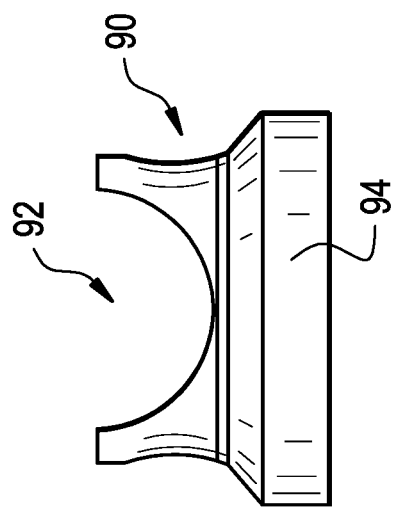
FIG. 5B illustrates a side view of the compression member shown in FIG. 5A.
Figure 5C:
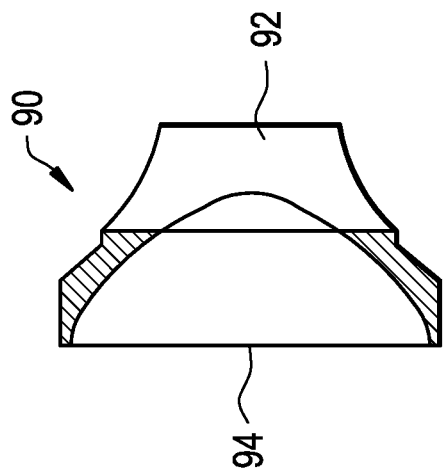
FIG. 5C illustrates a cross-section view of the compression member shown in FIG. 5A.

The bone anchor assembly 10 may optionally include a compression member 90 as shown in FIGS. 5A-C positionable within the receiver member 60 between the spinal connection element and the bone anchor. As illustrated in FIG. 1D, the compression member 90 may be positioned within the recess 68 between the spinal rod 80 and the head 42 of the shank 40. In the exemplary embodiment, the compression member 90 may have a proximal first surface 92 for engaging the spinal connection element and an opposing distal second surface 94 for engaging the head 42 of the shank.

The exemplary bone anchor assembly 10 may include a closure mechanism 100 that secures the spinal connection element to the bone anchor assembly. Referring to FIG. 1A, the closure mechanism 100 secures the exemplary spinal rod 80 within the recess 68 of the receiver member 60. The closure mechanism 100 may engage the first end 62 of the receiver member 60 or, in other exemplary embodiments, may engage other portion(s) of the receiver member 60. The exemplary closure mechanism 100 is an internal setscrew that engages an inner surface of the first end 62 of the receiver member 60. For example, the closure mechanism 100 may have external threads 102 that engage internal threads 104 provided on the first end 62 of the receiving member 60. Distal advancement of the closure mechanism 100 into engagement of the spinal rod 80, seats the spinal rod 80 in the proximal surface 22 of the compression member 90. The compression member 90 then is advanced onto the head 42 of the bone-engaging shank 40 advancing the head 42 against the inner surface of the insert 20 thereby fixing the relative movement of the head 42 in relation to the receiver member 60. In one embodiment, the major diameter of the bone-engaging shank 30 may be greater than the diameter of the closure mechanism 100 and the cylindrical opening 67 of the receiver member 60.

One skilled in the art will appreciate that other types of closure mechanisms may be employed. For example, an external closure mechanism positionable around the outer surface of the legs 76A, 76B of the receiving member 60 may be employed. In other exemplary embodiments, the closure mechanism may comprise an external and an internal closure mechanism, a non-threaded twist-in cap, and/or any other conventional closure mechanism.

Figure 6A:
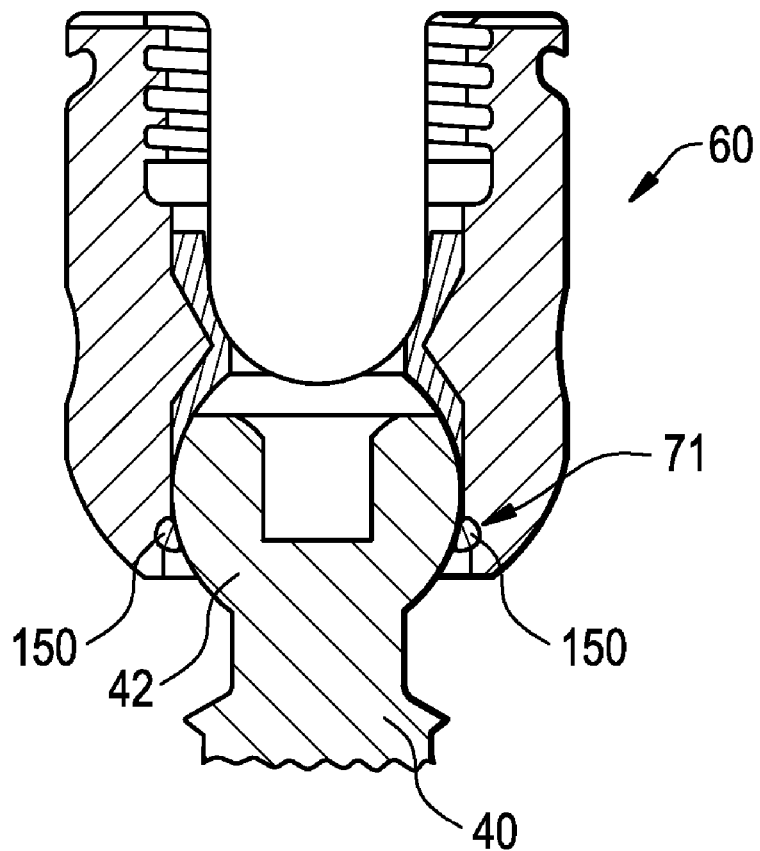
FIG. 6A illustrates a side view in cross section of another exemplary embodiment of a bone anchor assembly.
Figure 6B:
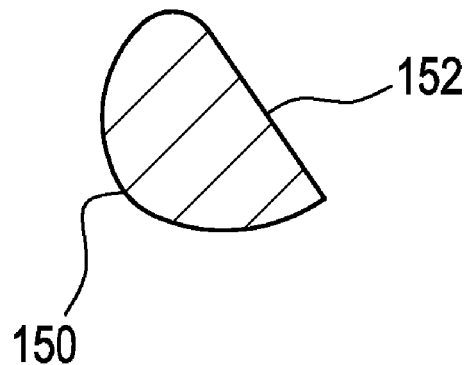
FIG. 6B illustrates a side view in cross section of the locking member of the bone anchor assembly of FIG. 6A.

FIGS. 6A & 6B illustrate an alternative embodiment of a bone anchor assembly in which locking member 150 forms a seat for the head 42 of the shank 40 within the receiver member 60. The locking member 150 may be positioned within a grove, hole, or the like provided within the receiving member 60. The locking member 150 may be arcuate, for example c-shaped, or, alternatively, may comprise multiple components to effectively provide a seat for the head 42. The locking member 150 may include a surface 152 configured to permit motion of the head 42 relative to the receiver member 60 such as in a ball and socket joint. For example the surface may be angled or arcuate to form a conical or spherical seat for head 42.

The components of the bone anchor assembly may be manufactured from any biocompatible material, including, for example, metals and metal alloys such as titanium and stainless steel, polymers, and/or ceramics. The components may be manufactured of the same or different materials. In one exemplary method of manufacturing, the bone-engaging shank 40, the retaining member 20, locking member 50 and the receiver member 60 are separately constructed and assembled prior to implantation. The head 42 of the shank 40 is inserted proximally through the bore 64 into the seat portion 72 of the receiver member 60. The retaining member 20 is advanced through the bore 64 around the head 42 of the shank into position within the seat portion 72. The locking member 50 is inserted through the opening 73 of the receiver member 60 and advanced through the groove 71 around the retaining member 20 to lock the retaining member 20 and the head 42 of the shank 40 within the seat portion 72 of the receiver member 60.

While the large diameter bone anchor assembly and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed:

1. A bone anchor assembly for engagement to a connection element comprising:
    a receiver member having an opening at the proximal end for receiving the connection element and a bore at the distal end, the receiver member having a seat portion having a groove provided within the distal end, between the opening and the bore, and being accessible from the bore;
    a bone-engaging shank having a generally spherically shaped head at a proximal end, the head sized to fit within the bore of the receiver member and having a generally hemispherically shaped distal surface;
    a retaining member interposed between the head of the shank and the bore at the distal end of the receiver member, the retaining member having an outer surface shaped to fit and positioned within the seat portion of the receiver member and a proximal inner surface shaped to accommodate the head of the bone-engaging shank, the distal surface of the head of the shank engaging the proximal inner surface of the retaining member to thereby retain the head within the receiver member; and
    a locking member shaped to fit and positioned within the groove of the seat portion to thereby lock the retaining member within the seat portion of the receiver member.

2. The bone anchor assembly of claim 1, wherein the retaining member has an inner surface generally spherical shaped to accommodate the head of the shank.

3. The bone anchor assembly of claim 1, wherein the receiver member has a second opening in a side wall of the receiver member for accessing the groove in the seat portion.

4. The bone anchor assembly of claim 1, wherein the groove has a semi-spherical shape.

5. The bone anchor assembly of claim 1, wherein the retaining member has a groove on the outer surface.

6. The bone anchor assembly of claim 5, wherein the groove of the retaining member aligns with the groove of the seat portion of the receiver member forming a channel.

7. The bone anchor assembly of claim 6, wherein the channel has a cylindrical shape.

8. The bone anchor assembly of claim 1, wherein the locking member is selected from the group comprising a wire, a cable, and a fiber.

9. The bone anchor assembly of claim 8, wherein the locking member has a generally elongated cylindrical shape.

10. The bone anchor assembly of claim 1, further comprising a compression member engaging the proximal end of the head of the shank and interposed between the connection element and the head when the connection element is engaged to the bone anchor assembly.

11. The bone anchor assembly of claim 1, further comprising a closure mechanism.

12. The bone anchor assembly of claim 11, wherein the diameter of the head of the shank is greater than the closure mechanism.

13. The bone anchor assembly of claim 11, wherein the major diameter of the shank is greater than the closure mechanism.

14. The bone anchor assembly of claim 1, wherein the major diameter of the shank is greater than the diameter of the opening of the receiver member.

15. A bone anchor assembly for engagement to a connection element comprising:
    a receiver member having an opening at the proximal end for receiving the connection element and a bore at the distal end leading to a seat portion having a groove, the opening including an internal thread having a minor diameter and a major diameter;
    a bone-engaging shank having a generally spherically shaped proximal head having a distal surface, the shank having an external thread having a major diameter greater than the minor diameter of the opening of the internal thread of the opening of the receiver member;
    a retaining member positioned within the seat portion of the receiver member having a proximal inner surface engaging the distal surface of the head of the shank; and
    a locking member positioned within the groove of the seat portion to thereby lock the retaining member within the seat portion of the receiver member.

* * * * *